United States Patent [19]

Ungerleider

[11] Patent Number: 5,372,577
[45] Date of Patent: Dec. 13, 1994

[54] APPARATUS FOR REDUCING INTRAOCULAR PRESSURE

[76] Inventor: Bruce A. Ungerleider, 511 66th St. N., St. Petersburg, Fla. 33710

[21] Appl. No.: 20,253

[22] Filed: Feb. 18, 1993

Related U.S. Application Data

[63] Continuation of Ser. No. 531,635, Jun. 1, 1990, abandoned, and a continuation of Ser. No. 179,671, Apr. 11, 1988, Pat. No. 4,936,825.

[51] Int. Cl.$^5$ .................................... A61M 27/00
[52] U.S. Cl. .................................... 604/8; 604/9
[58] Field of Search ............ 604/8, 9, 10, 294, 284, 604/264, 11; 623/4; 606/107

[56] References Cited

U.S. PATENT DOCUMENTS

| | | |
|---|---|---|
| 3,130,728 | 4/1964 | Pearson et al. |
| 3,159,161 | 12/1964 | Ness. |
| 3,788,327 | 1/1974 | Donowitz et al. |
| 3,915,172 | 10/1975 | Wichterle et al. ............ 604/8 |
| 3,948,272 | 4/1976 | Guibor. |
| 3,960,150 | 6/1976 | Hussain et al. ............ 604/294 X |
| 4,014,335 | 3/1977 | Arnold. |
| 4,402,681 | 9/1983 | Haas et al. |
| 4,428,746 | 1/1984 | Mendez. |
| 4,452,776 | 6/1984 | Refojo. |
| 4,457,757 | 7/1984 | Molteno. |
| 4,510,934 | 4/1985 | Batra. |
| 4,521,210 | 6/1985 | Wong. |
| 4,554,918 | 11/1985 | White. |
| 4,604,087 | 8/1986 | Joseph. |
| 4,634,418 | 1/1987 | Binder. |
| 4,713,075 | 12/1987 | Kurland. |
| 4,722,724 | 2/1988 | Schocket ............ 604/294 X |
| 4,729,761 | 3/1988 | White. |
| 4,750,901 | 6/1988 | Molteno ............ 604/8 |
| 4,767,400 | 8/1988 | Miller et al. ............ 604/8 |
| 4,787,885 | 11/1988 | Binder ............ 604/8 |
| 4,886,488 | 12/1989 | White ............ 604/9 |
| 4,915,684 | 4/1990 | Mackeen et al. ............ 604/294 X |
| 4,946,436 | 8/1990 | Smith ............ 604/8 |

Primary Examiner—Robert A. Hafer
Assistant Examiner—Sam Rimell
Attorney, Agent, or Firm—Frijouf, Rust & Pyle

[57] ABSTRACT

A method is described herein for implanting in the cornea and limbal area a device partially embedded and partially extending anteriorly, a preferred embodiment comprising one or more loops of small sized porous ropes, cords, bands or hollow tubes, which device has one end or section thereof extending beyond the exterior surface of the cornea and limbal areas so that aqueous humor may be exited from the anterior chamber in the eye to relieve intraocular pressure and thereby avoid or reduce the effects of glaucoma.

6 Claims, 3 Drawing Sheets

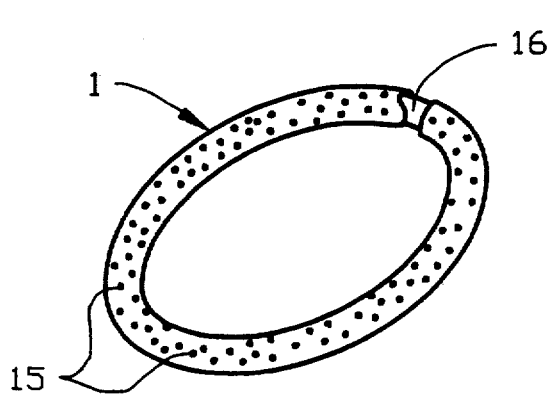
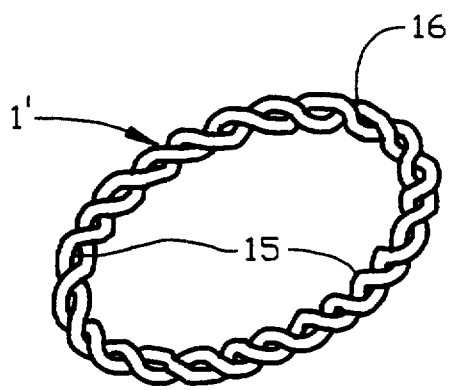
FIG. 3
FIG. 4
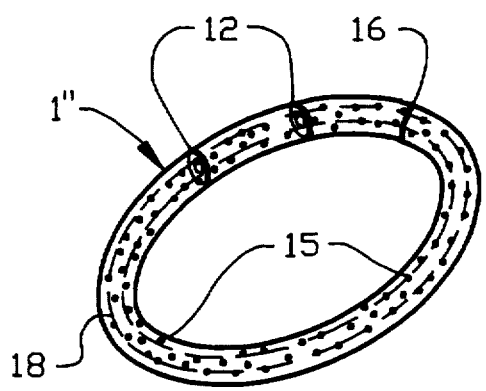
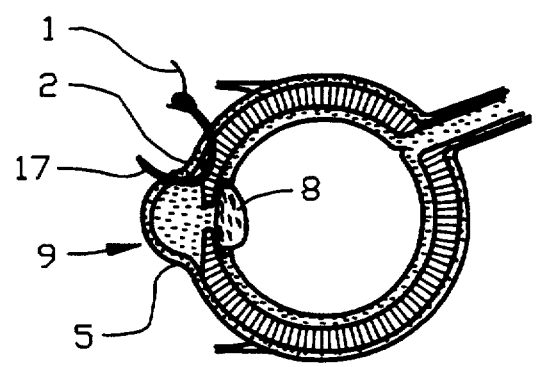
FIG. 5
FIG. 6
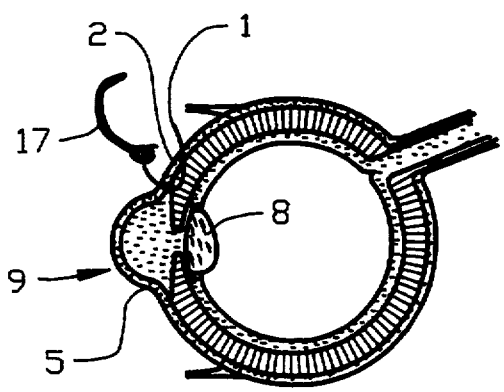
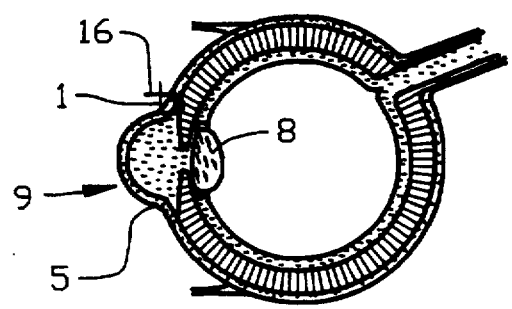
FIG. 7
FIG. 8

APPARATUS FOR REDUCING INTRAOCULAR PRESSURE

This application is a continuation of application Ser. No. 07/531,635 filed Jun. 1, 1990, now abandoned, the disclosure of which is incorporated herein by reference and a continuation of Ser. No. 07/179,671, filed Apr. 11, 1988, now U.S. Pat. No. 4,936,825.

BACKGROUND OF THE INVENTION

1. Field of the Invention

This invention relates to a method for implanting one or more porous devices, such as loops of small sized porous rope, cord or hollow tubes anterior to or under superficial layers of the cornea and limbal area with a portion of the loop of the porous material exiting on the ocular surface whereby ocular pressure is relieved by passage of aqueous humor through the device's porosity onto the eye's surface and thereby drained with the natural mechanism of tear fluid drainage. More specifically this invention relates to the method in which the pores in said porous material are small enough to prevent bacteria or other pathogen ingress.

2. State of the Prior Art

Glaucoma involves uncontrolled intraocular pressure within the eye caused by obstruction of aqueous outflow which may cause permanent damage to the optic nerve and retina. Surgical treatment of glaucoma has had limited success because of failure to control intraocular pressure as well as post-operative complications which may aggravate pre-operative increased intraocular pressure.

The eye is a complex organ. The cornea covers the front of the eye. Light is reflected by the cornea through the anterior chamber of the eye to the lens. The size of the entrance aperture of the eye, known as the pupil, is controlled by muscles. The lens is suspended by ciliary body zonules and focuses refracted light through the vitreous chamber onto the retina in the back of the eye. Ciliary muscles in the eye can vary the shape of the lens to focus on objects that are at various distances from the eye.

Aqueous humor is the fluid within the eye produced by the ciliary body, which fluid migrates through the pupil into the anterior chamber, through the trabecular meshwork and into veins which form aqueous fluid collection channels beneath the conjunctiva. When there is not sufficient aqueous humor outflow to relieve the intraocular pressure, glaucoma results.

Medical treatment of glaucoma has met with varying degrees of success. Eye drops, pills, and laser photocoagulation are used to reduce the production of aqueous humor in the ciliary body and to increase the outflow of aqueous fluid through the trabecular meshwork.

Surgical procedures of various types have also been attempted to improve the outflow-facility. These surgical techniques are generally unsuccessful due to post-operative scarring of the wound site itself or the overlying tissue planes, which scarring prevents adequate outflow of the aqueous humor out of the eye and results in a recurrence of the uncontrolled intraocular pressure.

Several U.S. patents have shown implantation devices involving hollow needles or tubes which require valves or other means to prevent bacterial ingress or must be completely imbedded in the eye or under tissue planes to avoid any exposure of a duct which will permit bacterial ingress. Such patents includes Pat. Nos. 3,159,161, 3,788,327, 4,402,681, 4,428,746 and 4,521,210. These devices are rigid and present possible discomfort as well as other problems.

A most recent operative treatment is the insertion of hydrogel setons in the space under the conjunctiva and/or contiguous tissue planes as described in U.S. Pat. No. 4,634,418 issued Jan. 6, 1987. However, this method, as described in col. 3, lines 45–47, states that the conjunctiva and/or contiguous tissue planes is closed over the entire surgical area to include the device. Therefore there is no provision for the aqueous humor to be exited directly unimpeded to the exterior of the eye. This distinction is important particularly since scarring of the conjunctival tissue and contiguous tissue planes can impede adequate egress of aqueous humor.

OBJECTIVES

It is an object of this invention to provide a method for enabling the exiting of aqueous humor from the interior to the exterior of the eye.

It is an object of this invention by means of this method of exiting aqueous humor to relieve the intraocular pressure which results in glaucoma.

It is also an object of this invention to provide such exiting means for aqueous humor by implanting below the superficial layers of the cornea and limbal area one or more porous devices, such as small sized porous ropes, cord or hollow tubes with an end of the device extending beyond the exterior surface of the cornea and limbal area.

Other objects of this invention will be apparent upon reading the disclosures herein.

SUMMARY OF THE INVENTION

In accordance with present invention, a method has been discovered which accomplishes the above objectives which comprises the implantation of one or more porous devices, such as loops of small sized porous ropes, cords or hollow tubes under the superficial layers of the cornea and limbal area with part of each such device, i.e., rope, cord or hollow tube, etc., extending to or beyond the exterior surface of the cornea whereby aqueous humor is permitted to pass through the porous device from the interior to the exterior of the cornea and limbal area thereby relieving the intraocular pressure caused by obstruction of the outflow facility. The porous materials used in the practice of this invention are of unclosed cell type so that liquid may pass from one pore to adjacent pores and thereby pass through the porous body of the device.

DESCRIPTION OF SPECIFIC EMBODIMENTS

The description of the method of this invention is facilitated by reference to the drawings.

FIG. 3 is a perspective view of a loop or continuous belt of a single filament of porous material.

FIG. 4 is a perspective view of a loop or continuous rope made of a number of intertwined filaments of porous material.

FIG. 5 is a perspective view of a loop or continuous hollow tube made of porous material.

FIG. 6 is a cross-sectional side view of the human eye with a needle attached to a loop as used in this invention and the needle being introduced into the cornea.

FIG. 7 is a cross-sectional side view of the portion of the eye into which the loop has been introduced as shown initiated in FIG. 6.

FIG. 8 is a cross-sectional side view of the portion of the eye into which the loop has been introduced and completed as shown initiated in FIG. 6.

Figure 1:
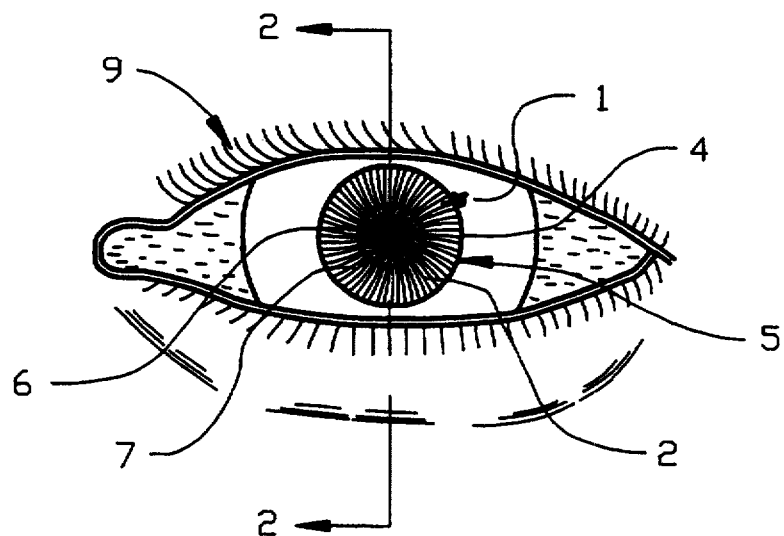
FIG. 1 is a front view of the human eye.
Figure 2:
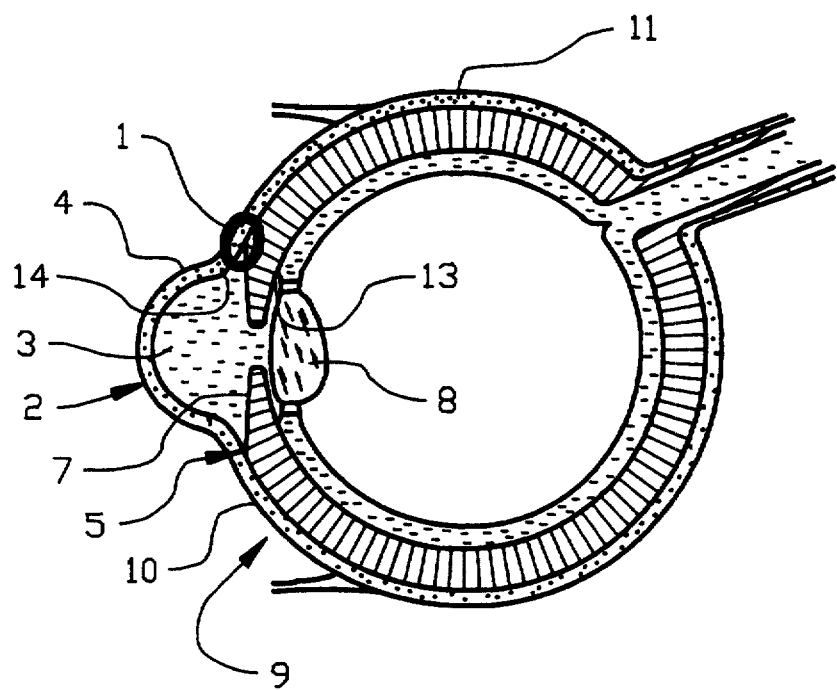
FIG. 2 is a cross-sectional side view taken at line 2—2 of FIG. 1.

As shown in FIGS. 1–5 a loop 1 of the types shown in FIGS. 3–5 is implanted beneath superficial layers of cornea 2 and limbal area 5 of eye 9 with a portion of loop 1 extending into the anterior chamber 3 with another portion of loop 1 extending onto the ocular surface 4 straddling the limbus 5. Pupil 6 is at the center of iris 7 by means of which the amount of light is controlled which passes to lens 8. Aqueous humor is passed through the small pores 15 of the loop device 1 and exit from an exterior portion thereof onto the ocular surface and is removed by the natural mechanism of tear fluid drainage. The conjunctiva 10, sclera 11, ciliary body 13 and filtration meshwork 14 are also shown in FIG. 2.

The loops of FIGS. 3–5 are made of a porous material 1 having tiny pores 15 through which the aqueous humor fluid may pass with the pores small enough to prevent bacteria and other pathogens ingress into the interior. The loops may be formed by tying or connecting together the ends of the strands of porous material 1. FIG. 5 shows a hollow type with the porous material exterior 1″ surrounding the hollow interior 18 with valves 12, such as shown in the prior art, for example, in U.S. Pat. No. 3,788,327, to prevent admission of bacteria and other pathogens.

One method of introducing the loops into the cornea 2 is shown in FIGS. 6–8. In FIG. 6 a slightly curved needle 17 fastened to the loop material 1 is introduced into the limbus 5 and cornea 2. In FIG. 7 the needle 17 is pulled through the cornea 2. In FIG. 8 the needle has been removed and the ends of the strand connected at 16 to form a loop.

As shown in these figures the loop device 1 has its posterior aspect in the anterior chamber and its anterior aspect on the ocular surface straddling the limbus 5 whereby excessive ocular pressure is relieved by passage of the aqueous humor through the porosity of the loop onto the eye's outer surface and thereby drained by natural mechanism of tear fluid drainage.

The porous material of the loops and other devices suitable for the practice of this invention is biocompatible with the tissue of the eye and may comprise as examples various plastic materials capable of forming pores of sufficient rigidity to retain their shape while performing their drainage function in the practice of this invention. The material should also be semi-rigid so as not to collapse under pressures exerted on it while in the eye. Typical materials may include but not limited to polyanhydrides, such as derived from bis(p-carboxyphenoxy)hexane and sebacic acid in various proportions, polyesters, polyamides, polyurethanes, polyacrylonitriles, polyphosphazenes, hydrogels, polymethylmethacrylate, cellulose acetate butyrate, silicone acrylate, polystyrene, silicone resins, fluoropolymers including Teflon, hydroxyethylmethacrylate, collagen and various other plastics and proteins.

There are numerous advantages to the method and device of this invention for treating glaucoma which include simplicity, easy insertion and easy removal of the porous loops, multiple placement in accordance with the number of such loops desired for the amount of fluid to be removed, self-regulation by pressure gradient developed, the intrinsic molecularly-based multiplicity of exit paths decreasing the risk of over or under filtration, the absence of open-ended tubular spaces prone to blockage and plugging, the absence of the need for unrealistic excessively precise mechanical fashioning, little likelihood of contiguous tissue injury, the greater flexibility of insertion site location, avoidance of retrograde bacteria and other pathogens movement into the eye by the small size of the pores and the natural pressure gradient of fluid flow from the inside to the outside of the eye, small chance for complications in view of the prior art, no complicated insertion technique required, and the avoidance of overlying tissue planes that scar down and impede fluid egress. Another advantage is the possibility that drugs for treatment of glaucoma may be allowed to seep in a reverse direction and fed into the eye.

The term "strand" of porous material is used herein to embrace the various porous ropes, cords, bands and hollow tubes described above. Moreover the expression "semi-rigid" means that the porous material is sufficiently rigid for the material to maintain the pores in an open condition and thereby permit the seeping, passage or flow of aqueous humor fluid therethrough.

While the strand is preferred in loop form for the practice of this invention, it is contemplated that the strand may also be unlooped form. However this leaves the ends of the strands subject to movement back and forth as the eyelids pass over the eye which may have an undesired effect even though the strand would still be capable of passing the aqueous humor as described above. Therefore in order to keep the exposed portions of the strand in a controlled or fixed position, it is preferred that the ends of the strand should be joined or connected to form a loop.

Figure 9:
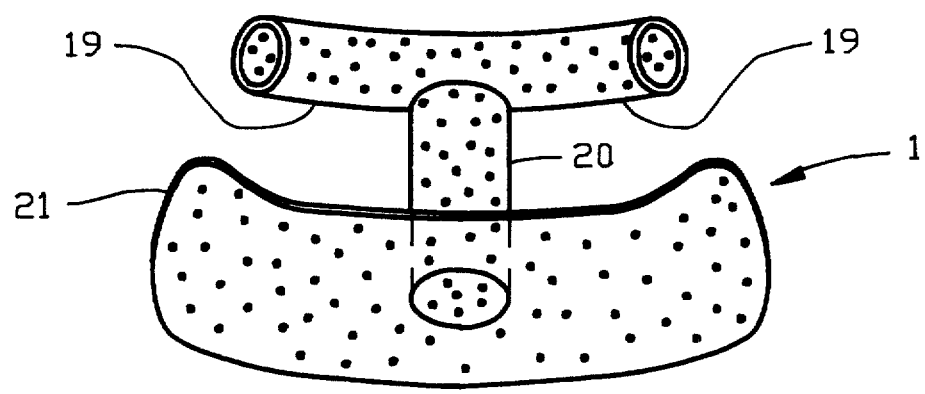
FIG. 9 is a perspective view of an alternative porous device suitable for the practice of this invention which comprises a curved cylindrical body to be embedded in the cornea layers and limbal area with a cylindrical feedoff from the first cylindrical body which connects to a substantially flat contact lens shape designed to fit over the outer surface of the cornea.
Figure 10:
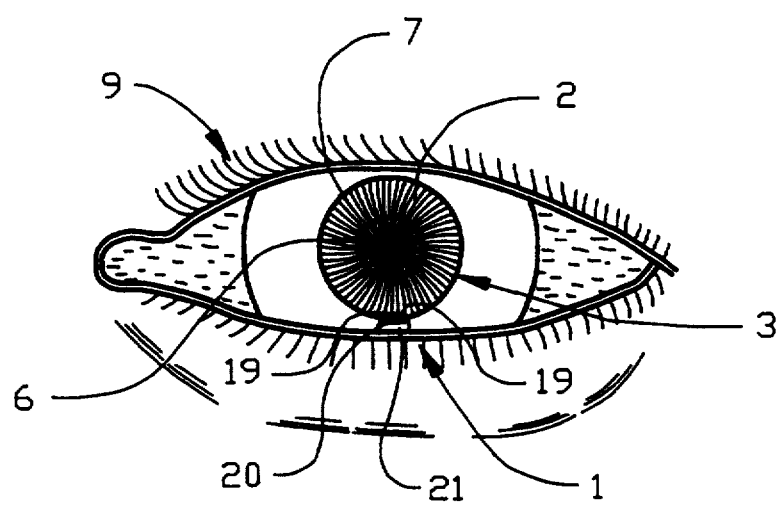
FIG. 10 is a front elevational view of the eye with the alternative porous device of FIG. 9 implanted through the cornea with the contact lens shape extending outside and adjacent to the exterior surface of the cornea.

Another form or modification of suitable porous device for the practice of this device is that shown in FIGS. 9 and 10 wherein a porous tubular device having an inner enlarged portion shown as cylindrical feet 19 joined vertically at its midsection with a central portion shown as a short central tube or cylindrical section 20 to an outer enlarged portion shown as a substantially thin concave section 21 shaped somewhat like a contact lens so as to fit the outer surface of the eye. Each of these sections is made of the porous material described herein so that when the cylindrical feet member 19 is implanted through the cornea and limbus area, the aqueous humor may seep into the interior and be passed through cylindrical section 20 to the concave surface member 21 where it may seep through the pores and exit on the outer surface of the eye.

For this type of device the preferred dimensions are about 2–15 mm. for the overall length of the cylindrical feet 19 with a diameter of about 1–4 mm., about 4 mm. length and 2–4 mm. diameter for the central tube 20 and a width of 2–10 mm. and length of about 2–20 mm. for the concave surface member 21.

For the porous devices used in the practice of this invention an effective pore size in the range of 50–1000 Angstrom units is found to be suitable.

As previously stated, the porous loops are the simplest of these devices and are the simplest to install.

While certain features of this invention have been described in detail with respect to various embodiments thereof, it will of course be apparent that other modifications can be made within the spirit and scope of this invention, and it is not intended to limit the invention to the exact details insofar as they are defined in the following claims.

The invention claimed is:

1. An apparatus for relieving the fluid pressure in the human eye associated with glaucoma, comprising:
   a strand defining an outer surface with said outer surface of said strand defining a first end, a middle and a second end;
   said strand being formed from an open celled biocompatible material and defining a plurality of pores defined therein with said plurality of pores communicating with adjacent pores for enabling liquid entering one portion of said outer surface of said strand to pass to other portions of said outer surface of said strand;
   said plurality of pores being sufficiently large for enabling the flow of aqueous humor therethrough and concomitantly sufficiently small to inhibit the ingress of pathogens therein;
   said strand being flexible and sufficiently rigid to maintain the size of said plurality of pores;
   said strand being implantable beneath the superficial layers of the cornea of the eye with the middle portion of said strand being disposed within the anterior chamber of the eye and straddling the limbus of the eye; and
   said first and second ends of said strand extending external to the eye and on the ocular surface of the eye for permitting aqueous humor fluid in the anterior chamber of the eye to pass from said middle portion of said strand through said plurality of pores in said strand and pass onto the ocular surface of the eye for relieving the fluid pressure in the eye associated with glaucoma; and
   means for connecting said first end of said strand directly to said second end of said strand external to the eye for maintaining the position of said strand within the eye, wherein said first and second ends are in direct contact.

2. An apparatus for relieving the fluid pressure in the human eye associated with glaucoma, comprising:
   a strand defining an outer surface with said outer surface of said strand defining a first end, a middle and a second end;
   said strand being formed from an open celled biocompatible material having a plurality of pores defined therein with said plurality of pores communicating with adjacent pores for enabling liquid entering one portion of said outer surface of said strand to pass to other portions of said outer surface of said strand;
   said plurality of pores being sufficiently large for enabling the flow of aqueous humor therethrough and concomitantly sufficiently small to inhibit the ingress of pathogens therein;
   said strand being flexible and sufficiently rigid to maintain the size of said plurality of pores;
   said strand being implantable beneath the superficial layers of the cornea of the eye with the middle portion of said strand being disposed within the anterior chamber of the eye and straddling the limbus of the eye;
   said first and second ends of said strand extending external to the eye and on the ocular surface of the eye for forming a loop with said strand for permitting aqueous humor fluid in the anterior chamber of the eye to pass from said middle portion of said strand through said plurality of pores in said strand and pass onto said ocular surface of the eye for relieving the fluid pressure in the eye associated with glaucoma; and
   means for joining said first end of said strand directly to said second end of said strand external to the eye for maintaining the position of said strand within the eye wherein said first and second ends are in direct contact.

3. An apparatus for introducing a drug from the ocular surface of the eye into anterior chamber of the eye, comprising:
   a strand defining an outer surface with said outer surface of said strand defining a first end, a middle and a second end;
   said strand being formed from an open celled biocompatible material and defining a plurality of pores therein with said plurality of pores communicating with adjacent pores for enabling liquid entering one portion of said outer surface of said strand to pass to other portions of said outer surface of said strand;
   said plurality of pores being sufficiently large for enabling the flow of aqueous humor therethrough and concomitantly sufficiently small to inhibit the ingress of pathogens therein;
   said strand being flexible and sufficiently rigid to maintain the size of said plurality of pores;
   said strand being implantable beneath the superficial layers of the cornea of the eye with the middle portion of said strand being disposed within the anterior chamber of the eye and straddling the limbus of the eye; and
   said first and second ends of said strand extending external to the eye and on the ocular surface of the eye for permitting aqueous humor fluid in the anterior chamber of the eye to pass from the middle portion of said strand through said plurality of pores in said strand and pass onto the ocular surface of the eye for relieving the fluid pressure in the eye associated with glaucoma and;
   means for connecting said first end of said strand directly to said second end of said strand external to the eye for maintaining the position of the strand within the eye and wherein said first and second ends are in direct contact, and;
   a drug disposed on the ocular surface of the eye for absorption by said plurality of pores to migrate through said plurality of pores in said body and to pass into the anterior chamber of the eye.

4. An apparatus for transferring aqueous humor from the anterior chamber of the eye onto the ocular surface, comprising:
   a body defining an outer surface;
   said body having an inner enlarged portion and an outer enlarged portion with a central portion disposed therebetween;

said inner enlarged portion and said outer enlarged portion being substantially enlarged relative to said central portion with said inner and outer enlarged portions extending substantially perpendicular to said central portion, said inner enlarged portion defining cylindrical feet and said outer enlarged portion defining a concave surface;

said body having a plurality of pores defined therein with said plurality of pores communicating with adjacent pores for enabling liquid entering one portion of said outer surface of said body to pass to other portions of said outer surface of said body;

said plurality of pores being sufficiently large for enabling the flow of aqueous humor therethrough and concomitantly sufficiently small to inhibit the ingress of pathogens therein;

said body being flexible and sufficiently rigid to maintain the size of said plurality of pores; and said inner enlarged portion of said body member being implanted beneath the superficial layers of the cornea of the eye and in communication with the anterior chamber and straddling the limbus of the eye and with said outer enlarged portion being disposed proximate to the ocular surface of the eye for permitting aqueous humor fluid in the anterior chamber of the eye to pass through said plurality of pores in said body and pass onto the ocular surface of the eye.

5. An apparatus for transferring aqueous humor from the anterior chamber of the eye onto the ocular surface, comprising:

a body defining an outer surface;

said body having an inner enlarged portion and an outer enlarged portion with a central portion disposed therebetween;

said central portion of said body being substantially cylindrical;

said inner enlarged portion and said outer enlarged portion being substantially enlarged relative to said central portion with said inner and outer enlarged portions extending substantially perpendicular to said central portion, said inner enlarged portion defining cylindrical feet and said outer enlarged portion defining a concave surface;

said body having a plurality of pores defined therein with said plurality of pores communicating with adjacent pores for enabling liquid entering one portion of said outer surface of said body to pass to other portions of said outer surface of said body;

said plurality of pores being sufficiently large for enabling the flow of aqueous humor therethrough and concomitantly sufficiently small to inhibit the ingress of pathogens therein;

said body being flexible and sufficiently rigid to maintain the size of said plurality of pores; and said inner enlarged portion of said body member being implanted beneath the superficial layers of the cornea of the eye and in communication with the anterior chamber and straddling the limbus of the eye and with said outer enlarged portion being disposed proximate to the ocular surface of the eye for permitting aqueous humor fluid in the anterior chamber of the eye to pass through said plurality of pores in said body and pass onto the ocular surface of the eye.

6. An apparatus for introducing a drug into an anterior chamber of the eye, comprising:

a strand defining an outer surface with said outer surface of said strand defining a first end, a middle and a second end;

said strand being formed from an open celled biocompatible material and defining a plurality of pores therein with said plurality of pores communicating with adjacent pores for enabling liquid entering one portion of said outer surface of said strand to pass to other portions of said outer surface of said strand;

said plurality of pores being sufficiently large for enabling the flow of aqueous humor therethrough and concomitantly sufficiently small to inhibit the ingress of pathogens therein;

said strand being flexible and sufficiently rigid to maintain the size of said plurality of pores;

said strand being implantable beneath the superficial layers of the cornea of the eye with the middle portion of said strand being disposed within the anterior chamber of the eye and straddling the limbus of the eye; and said first and second ends of said strand extending external to the eye and on the ocular surface of the eye for permitting aqueous humor fluid in the anterior chamber of the eye to pass from the middle portion of said strand through said plurality of pores in said strand and pass onto the ocular surface of the eye for reliving the fluid pressure in the eye associated with glaucoma and;

means for connecting said first end of said strand directly to said second end of said strand external to the eye for maintaining the position of the strand within the eye and wherein said first and second ends are in direct contact, and;

a drug located in said plurality of pores of said body.

* * * * *